US011903390B1

(12) United States Patent
El Sherif et al.

(10) Patent No.: US 11,903,390 B1
(45) Date of Patent: Feb. 20, 2024

(54) **ENHANCED *CURCUMA LONGA* PRODUCTIVITY AND MEDICINAL VALUES BY USING *MORINGA OLEIFERA* LEAF EXTRACT**

(71) Applicant: KING FAISAL UNIVERSITY, Al-Ahsa (SA)

(72) Inventors: Fadia El Sherif, Al-Ahsa (SA); Salah Khattab, Al-Ahsa (SA); Alaa Ahmed Ali Alamer, Al-Ahsa (SA); Yun Kiam Yap, Shanghai (CN)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/242,083

(22) Filed: Sep. 5, 2023

(51) Int. Cl.
*A01N 65/00* (2009.01)
*A61K 36/9066* (2006.01)
*A01P 21/00* (2006.01)
*A01N 65/08* (2009.01)

(52) U.S. Cl.
CPC .............. *A01N 65/08* (2013.01); *A01P 21/00* (2021.08); *A61K 36/9066* (2013.01)

(58) Field of Classification Search
CPC ...... A01N 65/08; A01P 21/00; A61K 36/9066
See application file for complete search history.

(56) References Cited

U.S. PATENT DOCUMENTS

| 9,388,343 B2 | 7/2016 | Rehage |
| 11,122,809 B2 * | 9/2021 | Radhakrishnan ........ C05G 5/30 |
| 2004/0156920 A1 | 8/2004 | Kane |

FOREIGN PATENT DOCUMENTS

| CN | 111195269 A | 5/2020 |
| CN | 107541332 B | 5/2021 |

OTHER PUBLICATIONS

Al-Abbas et al., Plant Archives, 2019, 19, 1247-1258.*
Hossain et al., Plant Prod Sci, 2005, 8(1), 86-94.*
Culver, M. et al., "Effect of Moringa Extract on Growth and Yield of Tomato", Greener Journal of Agricultural Sciences 2(5): pp. 207-211 2012.
Kanchani, A. & Harris, K.D., "Effects of Foliar Application of Moringa (*Moringa oleifera*) Leaf Extract with Recommended Fertilizer on Growth and Yield of Okra (*Abelmoschus esculentus*)", Journal of Agricultural Sciences AGRIEAST 13(2): pp. 38-54 (2019).
Al Dayel, M.F. & El Sherif, F., "Spirulina platensis Foliar Spraying Curcuma longa Has Improved Growth, Yield, and Curcuminoid Biosynthesis Gene Expression, as Well as Curcuminoid Accumulation", Horticulturae 8(6): 469 (2022).

* cited by examiner

*Primary Examiner* — Kyle A Purdy
(74) *Attorney, Agent, or Firm* — Nath, Goldberg & Meyer; Richard C. Litman

(57) ABSTRACT

Methods for stimulating the growth, yield, and secondary metabolite production of *Curcuma longa* plants are provided. Administration of between about 2.5 mg/L and about 10 mg/L *Moringa oleifera* extract to *Curcuma longa* plants results in increased plant growth, rhizome production, and production of secondary metabolites including curcuminoids.

4 Claims, No Drawings

ENHANCED *CURCUMA LONGA* PRODUCTIVITY AND MEDICINAL VALUES BY USING *MORINGA OLEIFERA* LEAF EXTRACT

BACKGROUND

1. Field

The disclosure of the present patent application relates to compositions and methods for administering a biostimulant to *Curcuma longa*, and particularly to compositions and methods for administering *Moringa oleifera* extract to enhance *Curcuma longa* growth and production of secondary metabolites by *Curcuma longa*.

DESCRIPTION OF THE PRIOR ART

The use of chemical fertilizers and pesticides to increase crop growth and yield have further aggravated crop production problems as they have led to nitrate pollution of the ground water, nutrient imbalance of the soil, and short- and/or long-term health threats to the whole biosphere. In view of this, the development of bio-stimulants has gaining popularity over recent decades. Over the last decade, fertilizers of biological origin have gained popularity due to their environmentally friendly nature. Extracts from plants and algae are among those bio-fertilizers as they contain essential elements that support plant growth.

*Moringa oleifera* leaf is rich in minerals, fibers, proteins, sugars, free proline, free amino acids, vitamins, phytohormones, and antioxidants. Its extract prepared in ethanol or water is low cost and environmentally friendly.

*Curcuma longa* is an herbaceous perennial plant. The underground portion of *Curcuma longa* contains the rhizomes, which are used as spices and as traditional therapeutic remedies for treating various illnesses such as digestive and respiratory disorders, arthritis and rheumatism, and aiding wound healing. Curcuminoid is a phenolic compound composed of curcumin and its derivatives, dimethoxy curcumin and bis-demethoxy curcumin, found in the rhizomes. Curcuminoid has been implicated in the antioxidant, anti-inflammatory, antimutagenic, antimicrobial, and anticancer activities of turmeric extracts.

Curcumin is characterized by a comprehensive range of biological, medicinal, and pharmacological activities. Curcumin has been demonstrated to have antioxidant, antimicrobial, anti-malarial, antimutagenic, anticancer, anti-thrombotic, anti-hyperlipidemic, hypoglycemic, anti-inflammatory, anti-rheumatic, and myocardial infarction protective activities. Such properties have been associated with the secondary metabolites present in the rhizomes.

Thus, compositions and methods to solve the aforementioned problems are desired.

SUMMARY

The present subject matter relates to the use of *Moringa oleifera* extracts as biostimulants and/or biofertilizers to increase the growth and secondary metabolite production of *Curcuma longa*.

Accordingly, in one embodiment, the present subject matter relates to a method of administering a biostimulant composition comprising *Moringa oleifera* extract to *Curcuma longa* to increase the growth of *Curcuma longa*. The *Moringa oleifera* extract may be *Moringa oleifera* leaf extract and it may be administered by foliar spraying. The administration of the *Moringa oleifera* extract may result in increased shoot length, root length, number of roots, and number of leaves of, e.g., *C. longa*.

In another embodiment, the present subject matter relates to a method of administering a biostimulant composition comprising *Moringa oleifera* extract to *Curcuma longa* to increase the rhizome production of *Curcuma longa*. The *Moringa oleifera* extract may be *Moringa oleifera* leaf extract and it may be administered by foliar spraying. The administration of the *Moringa oleifera* extract may result in an increase in the number of rhizomes, diameter of rhizomes, dry weight of leaves, dry weight of roots, and dry weight of rhizomes of the *Curcuma longa*.

In a further embodiment, the present subject matter relates to a method of administering a biostimulant composition comprising *Moringa oleifera* extract to *Curcuma longa* to increase the secondary metabolite production of *Curcuma longa*. The *Moringa oleifera* extract may be *Moringa oleifera* leaf extract and it may be administered by foliar spraying. The administration of the *Moringa oleifera* extract may result in increased secondary metabolite production of *Curcuma longa*, including but not limited to production of bisdemethoxycurcumin, demethoxycurcumin, and curcumin.

These and other features of the present subject matter will become readily apparent upon further review of the following specification.

DETAILED DESCRIPTION

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine or pigs, horses, camels, poultry, rabbits, goats, dogs, cats, and the like.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

As used herein, the term "about", when modifying a number, shall mean within a range of up to 10% above or below the modified value.

The present subject matter relates to the use of *Moringa oleifera* extracts as biostimulants to increase the growth and secondary metabolite production of *Moringa oleifera*.

Accordingly, in an embodiment, the biostimulant composition comprises between about 2.5 mg/L and about 10 mg/L *Moringa oleifera* extract (MLE) diluted in ethanol. In another embodiment, the biostimulant composition comprises about 2.5 mg/L about 5 mg/L, or about 10 mg/L MLE diluted in ethanol.

In an embodiment, the biostimulant composition may be administered to the *Curcuma* long plants by foliar spraying.

The biostimulant compositions described herein can be prepared by mixing LE with appropriate volumes of 20% ethanol. For example, the method of making a biostimulant composition herein can include obtaining *Moringa oleifera* extract by air drying leaves of an *Moringa oleifera* plant, grinding them into powder, mixing the *Moringa oleifera* powder with 80% ethanol to obtain a suspension, swirling the suspension, filtering the suspension to obtain a filtrate, drying the filtrate to obtain a dried filtrate, and resuspending the dried filtrate in 20% ethanol to obtain the *Moringa oleifera* extract (MLE). The MLE may be stored at 4° C. until use, or overnight.

The composition can be presented in a form suitable for daily, weekly, monthly, bi-monthly, or any desired schedule of administration. The compositions herein can contain, per dosage unit, amounts of the active ingredients necessary to deliver an effective dose. Effective amounts of the MLE may be determined initially from the Examples described herein and adjusted for specific *Curcuma longa* growth conditions using routine methods.

In an embodiment, the composition can be presented in a form suitable for administration on the $4^{th}$, $6^{th}$, and $8^{th}$ month after planting of *Curcuma longa* rhizomes.

In a further embodiment, the present subject matter relates to a method of administering a biostimulant composition comprising *Moringa oleifera* extract to *Curcuma longa* to increase the growth of *Curcuma longa*. The MLE may be *Moringa oleifera* leaf extract and it may be administered by foliar spraying. The administration of the MLE may result in an increase of at least one measure of plant growth selected from the group consisting of shoot length, root length, number of roots, and number of leaves.

The administration of MLE at about 2.5 mg/L may result in an increase in the shoot length, root length, number of roots, and number of leaves of *C. longa*.

The administration of MLE at about 5 mg/L may result in an increase in the shoot length, root length, number of roots, and number of leaves of *C. longa*.

The administration of MLE at about 10 mg/L may result in an increase in the shoot length, root length, number of roots, and number of leaves of *C. longa*.

In another embodiment, the present subject matter relates to a method of administering a biostimulant composition comprising *Moringa oleifera* extract to *Curcuma longa* to increase the rhizome production of *Curcuma longa*. The *Moringa oleifera* extract may be *Moringa oleifera* leaf extract and it may be administered by foliar spraying. The administration of the *Moringa oleifera* extract may result in increase in at least one metric selected from the group consisting of number of rhizomes, diameter of rhizomes, dry weight of leaves, dry weight of roots, and dry weight of rhizomes.

The administration of MLE at about 2.5 mg/L may result in an increase in the number of rhizomes, the diameter of the rhizomes, the dry weight of leaves, the dry weight of roots, and the dry weight of rhizomes of *C. longa*.

The administration of MLE at about 5 mg/L may result in an increase in the number of rhizomes, the diameter of the rhizomes, the dry weight of leaves, the dry weight of roots, and the dry weight of rhizomes of C. longa.

The administration of MLE at about 10 mg/L may result in an increase in the number of rhizomes, the diameter of the rhizomes, the dry weight of leaves, and the dry weight of roots of C. longa.

In a further embodiment, the present subject matter relates to a method of administering a biostimulant composition comprising Moringa oleifera extract to Curcuma longa to increase the secondary metabolite production of Curcuma longa. The Moringa oleifera extract may be Moringa oleifera leaf extract and it may be administered by foliar spraying. The administration of the Moringa oleifera extract may result in increased secondary metabolite production of Curcuma longa, including but not limited to production of bisdemethoxycurcumin, demethoxycurcumin, and curcumin.

The administration of MLE at about 2.5 mg/L may result in an increase in the production of bisdemethoxycurcumin, demethoxycurcumin, and curcumin by C. longa.

The administration of MLE at about 5 mg/L may result in an increase in the production of bisdemethoxycurcumin, demethoxycurcumin, and curcumin by C. longa.

The administration of MLE at about 10 mg/L may result in an increase in the production of bisdemethoxycurcumin, demethoxycurcumin, and curcumin by C. longa.

The present subject matter may be further understood in view of the following examples.

EXAMPLES

Example 1

Moringa oleifera was gathered from the AL Sahab farm, Al-Ahsa, Kingdom of Saudi Arabia. Moringa leaves were harvested from 4 year old plants. The Moringa oleifera leaf extract was prepared by ethanol extraction (modified from Makkar & Becker, 1996). Young Moringa leaves were air-dried, and ground into powder form. Subsequently, 20 g of Moringa leaf powder was mixed with 675 mL of 80% ethanol, and the suspension was swirled at 200 rpm for 3 days. The suspension was then filtered with filter paper, and the filtrate was dried in a fume hood. The dried filtrate was finally resuspended in appropriate volumes of 20% ethanol to achieve the 2.5-, 5-, and 10 mg/L leaf extracts.

The MLE at the above concentrations were prepared and stored at 4° C. a night before use. Tween 80 at a final concentration of 0.5% was added to each spray solution before the application. Foliar spraying was performed three times (on the 4th-, 6th-, and 8th months after the planting of the Curcuma rhizomes). Curcuma plants were sprayed between 9 and 10 am. The whole aerial part of the Curcuma plant was sprayed with the respective treatment solution to ensure that all the leaves area were moistened by the sprayed solutions.

The effects of ALE treatments on Curcuma longa growth were assessed by measuring shoot length, root length, number of roots, and number of leaves of Curcuma longa plants treated with 2.5 mg/L, 5 mg/L, and 10 mg/L MLE. The results are summarized in Table 1.

TABLE 1

Superscripts indicate significant differences.

| Treatment | Shoot length (cm) | Root length (cm) | Number of roots (n) | Number of leaves (n) |
|---|---|---|---|---|
| Control | $97.50^{bc*}$ | $12.25^{cd}$ | $20.75^{d}$ | $9.50^{abc}$ |
| MLE 2.5 mg/L | $116.00^{ab}$ | $15.67^{abc}$ | $29.00^{bc}$ | $10.00^{abc}$ |
| MLE 5 mg/L | $130.50^{a}$ | $18.25^{a}$ | $34.00^{ab}$ | $10.00^{abc}$ |
| MLE 10 mg/L | $109.75^{ab}$ | $13.25^{bcd}$ | $25.25^{cd}$ | $10.75^{a}$ |

The effects of MLE treatments on Curcuma longa rhizome production were assessed by measuring number of rhizomes, rhizome diameter, dry weight of leaves, dry weight of roots, and dry weight of rhizomes of Curcuma longa plants treated with 2.5 mg/L, 5 mg/L, and 10 mg/L MLE. The results are summarized in Table 2.

TABLE 2

Superscripts indicate significant differences.

| Treatment | Number of rhizomes (n) | Rhizome's diam. (mm) | Leaves dry weight (g) | Roots dry weight (g) | Rhizomes dry weight (g) |
|---|---|---|---|---|---|
| Control | $3.25^{c*}$ | $14.58^{b}$ | $9.60^{b}$ | $0.83^{c}$ | $11.35^{b}$ |
| MLE 2.5 mg/L | $9.67^{a}$ | $19.67^{ab}$ | $18.83^{a}$ | $1.43^{bc}$ | $19.67^{ab}$ |
| MLE 5 mg/L | $6.25^{bc}$ | $20.86^{a}$ | $21.85^{a}$ | $1.73^{ab}$ | $27.10^{a}$ |
| MLE 10 mg/L | $4.25^{bc}$ | $16.09^{ab}$ | $10.85^{b}$ | $1.23^{bc}$ | $11.55^{b}$ |

The effects of MLE treatments on Curcuma longa secondary metabolite production were assessed by measuring the amount of bisdemethoxycurcumin, demethoxycurcumin, and curcumin produced by Curcuma longa plants treated with 2.5 mg/L, 5 mg/L, and 10 mg/L MLE. The results are summarized in Table 3.

TABLE 3

Superscripts indicate significant differences.

| Treatment | Bisdemethoxy-curcumin (ug/mL) | Demethoxy-curcumin (ug/mL) | Curcumin (ug/mL) |
|---|---|---|---|
| Control | $293.796^{d*}$ | $180.199^{e}$ | $617.604^{f}$ |
| MLE 2.5 mg/L | $364.529^{cd}$ | $316.262^{d}$ | $874.394^{e}$ |
| MLE 5 mg/L | $533.799^{a}$ | $456.492^{b}$ | $1231.590^{ab}$ |
| MLE 10 mg/L | $512.455^{a}$ | $394.804^{c}$ | $1109.218^{c}$ |

As indicated in the results shown in Tables 1, 2 and 3, it was found that the application of Moringa oleifera leaf extract at all three concentrations improved plant growth (increase in length of shoot and root, and number of roots and leaves) and yield (increase in number of rhizomes, rhizome's diameter, and dried weight of leaves, roots, and rhizomes). In addition, increase in all three components of the Curcuma active compounds, curcuminoid (Bisdemethoxycurcumin, Demethoxycurcumin, and Curcumin) was observed.

It is to be understood that the biostimulant for enhancing Curcuma longa growth and secondary metabolite production is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of enhancing secondary metabolite production of a *Curcuma longa* plant, the method comprising administering a biostimulant to the *Curcuma longa* plant, wherein the biostimulant comprises *Moringa oleifera* extract and wherein the administration of the biostimulant results in an increase in at least one measure of secondary metabolite production of the *Curcuma longa* plant; wherein the at least one measure of secondary metabolite production of the *Curcuma longa* plant is selected from the group consisting of bisdemethoxycurcumin, demethoxycurcumin, and curcumin production of the *Curcuma longa* plant.

2. The method of claim 1, comprising administering the biostimulant to the *Curcuma longa* plant by foliar spraying.

3. The method of claim 1, comprising administering between about 2.5 mg/L and about 10 mg/L *Moringa oleifera* extract to the *Curcuma longa* plant.

4. The method of claim 3, comprising administering about 10 mg/L *Moringa oleifera* extract to the *Curcuma longa* plant.

* * * * *